(12) United States Patent
Wang et al.

(10) Patent No.: US 12,214,006 B2
(45) Date of Patent: Feb. 4, 2025

(54) TRADITIONAL CHINESE MEDICINE OINTMENT FOR PREVENTING AND TREATING MASTITIS IN DAIRY COWS, AND PREPARATION METHOD THEREOF

(71) Applicant: Hunan University of Science and Engineering, Hunan (CN)

(72) Inventors: Zongcheng Wang, Hunan (CN); Yuanfei Xu, Hunan (CN); Zuodong Qin, Hunan (CN); Zhenmin Cao, Hunan (CN); Xiaofang Luo, Hunan (CN); Chen Gui, Hunan (CN); Shuwen Wang, Hunan (CN); Asad Nawaz, Hunan (CN); Manting Li, Hunan (CN)

(73) Assignee: Hunan University of Science and Engineering, Hunan (CN)

( * ) Notice: Subject to any disclaimer, the term of this patent is extended or adjusted under 35 U.S.C. 154(b) by 0 days.

(21) Appl. No.: 18/467,250

(22) Filed: Sep. 14, 2023

(65) Prior Publication Data
US 2024/0100112 A1 Mar. 28, 2024

(30) Foreign Application Priority Data
Sep. 22, 2022 (CN) .......................... 202211157538.4

(51) Int. Cl.
| | | |
|---|---|---|
| A61K 36/288 | (2006.01) | |
| A61K 9/06 | (2006.01) | |
| A61K 31/045 | (2006.01) | |
| A61K 36/35 | (2006.01) | |
| A61K 36/355 | (2006.01) | |
| A61K 38/10 | (2006.01) | |
| A61K 47/14 | (2017.01) | |
| A61K 47/44 | (2017.01) | |
| A61P 31/04 | (2006.01) | |

(52) U.S. Cl.
CPC .............. *A61K 36/288* (2013.01); *A61K 9/06* (2013.01); *A61K 31/045* (2013.01); *A61K 36/35* (2013.01); *A61K 36/355* (2013.01); *A61K 38/10* (2013.01); *A61K 47/14* (2013.01); *A61K 47/44* (2013.01); *A61P 31/04* (2018.01); *A61K 2236/333* (2013.01)

(58) Field of Classification Search
CPC ........ A61K 9/06; A61K 31/10; A61K 36/288; A61K 31/045; A61K 36/35; A61K 36/355; A61K 38/10; A61K 47/14; A61K 47/44; A61K 2236/333; A61P 31/04
See application file for complete search history.

(56) References Cited

U.S. PATENT DOCUMENTS

2019/0336568 A1  11/2019  Luo et al.

FOREIGN PATENT DOCUMENTS

| CN | 1660209 A | * | 8/2005 | |
|---|---|---|---|---|
| CN | 1965976 A | | 5/2007 | |
| CN | 101342243 A | | 1/2009 | |
| CN | 102038748 A | | 5/2011 | |
| CN | 102716431 A | | 10/2012 | |
| CN | 102793780 A | | 11/2012 | |
| CN | 104983815 A | | 10/2015 | |
| CN | 105106215 A | | 12/2015 | |
| CN | 106496306 A | | 3/2017 | |
| CN | 107095940 A | | 8/2017 | |
| JP | 6359630 B2 | * | 7/2018 | ........... A61K 31/787 |
| RU | 2706689 C1 | | 11/2019 | |
| WO | 2021158517 A1 | | 8/2021 | |

OTHER PUBLICATIONS

Gong et al. (The Herba Patriniae (Caprifoliaceae): A review on traditional uses, phytochemistry, pharmacology and quality control, J Ethnopharmacol, Aug. 23, 2020, 265: 113264,pp. 1-35). (Year: 2020).*
Hao Jingfeng et al., "Comparison of in Vitro Bacteriostasis Effects of 20 Traditional Chinese Medicines on Three Pathogenic Bacteria of Subclinical Mastitis in Dairy Cow," Chinese Journal of Veterinary Medicine, Feb. 2017, pp. 55-58.
Wang Yu et al., "Drug Sensitivity Test of Dandelion to Bacteria-caused Mastitis in Dairy Cows," Breeding and feed, May 2015.
Ou Deyuan et al., "Study on the effect of compound traditional Chinese medicine ointment on clinical mastitis of dairy cows," Guizhou Animal Husbandry and Veterinary, Aug. 2012.
Bai Dongdong et al., "Research progress on clinical effect and mechanism of traditional Chinese medicine in treating mastitis in dairy cows," Progress in Veterinary Medicine, Oct. 2018, pp. 91-95, vol. 39, No. 10.
First Search Report for China Application No. 202211157538.4.
Supplemental Search Report for China Application No. 202211157538.4.

(Continued)

*Primary Examiner* — Aaron J Kosar
*Assistant Examiner* — Jacob A Boeckelman

(57) ABSTRACT

Provided are a traditional Chinese medicine ointment for preventing and treating mastitis in dairy cows and a preparation method thereof, belonging to the technical field of veterinary traditional Chinese medicines. The traditional Chinese medicine ointment includes raw materials in parts by mass: 20-30 parts of dandelion, 20-30 parts of herba patriniae, 10-16 parts of Caulis Lonicerae Japonicae, 0.5-1 part of borneol, 0.03-0.05 part of polypeptide, 40-50 parts of auxiliary emulsifier, 40-50 parts of liquid paraffin and 100-130 parts of white vaseline. An amino acid sequence of the polypeptide is: Phe Phe Arg Lys Val Leu Lys Leu Ile Arg Lys Ile Trp Arg (SEQ ID NO. 1). In the application, dandelion, herba patriniae, Caulis Lonicerae Japonicae and borneol 1 are mixed, and polypeptide is added at the same time to prepare ointment.

3 Claims, 1 Drawing Sheet

Specification includes a Sequence Listing.

(56) References Cited

OTHER PUBLICATIONS

Office Action for China Application No. 202211157538.4, mailed Mar. 16, 2023.
Notice to Grant for China Application No. 202211157538.4, mailed May 2, 2023.

* cited by examiner

```
┌─────────────────────────────────────────────────────────────┐
│ Adding the dandelion, the herba patriniae and the Caulis Lonicerae Japonicae │──── S1
│ into ethanol aqueous solution, extracting, and concentrating to obtain       │
│ traditional Chinese medicine concentrated solution                            │
└─────────────────────────────────────────────────────────────┘
                              │
                              ▼
┌─────────────────────────────────────────────────────────────┐
│ Grinding the borneol and part of the liquid paraffin to eutectic; adding    │──── S2
│ remaining liquid paraffin and molten-state white vaseline, keeping a         │
│ temperature, adding the auxiliary emulsifier, stirring well, adding the      │
│ traditional Chinese medicine concentrated solution and the polypeptide,      │
│ homogenizing, and cooling to obtain the traditional Chinese medicine         │
└─────────────────────────────────────────────────────────────┘
```

TRADITIONAL CHINESE MEDICINE OINTMENT FOR PREVENTING AND TREATING MASTITIS IN DAIRY COWS, AND PREPARATION METHOD THEREOF

CROSS-REFERENCE TO RELATED APPLICATIONS

This application claims priority of Chinese Patent Application No. 202211157538.4, filed on Sep. 22, 2022, the entire contents of which are incorporated herein by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:
File name: sequence_347_059_PPH_9630. xml
Creation date: 24 Aug. 2023
Byte size: 1,822 bytes

TECHNICAL FIELD

The application relates to the technical field of veterinary traditional Chinese medicine, and in particular to a traditional Chinese medicine ointment for preventing and treating mastitis in dairy cows and a preparation method thereof.

BACKGROUND

Mastitis in dairy cows is the most serious disease among the four major diseases: breast disease, reproductive disease, limb and hoof disease and metabolic disease. It is a very difficult and common disease encountered by dairy farmers in the process of dairy farming, which has brought serious harm and loss to dairy production. Mastitis in dairy cows is clinically divided into clinical mastitis and recessive mastitis. The main pathogenic microorganisms are *Escherichia coli, Staphylococcus aureus* and *Streptococcus*.

For many years, antibiotics have been the first choice for the treatment of mastitis in dairy cows. However, long-term repeated use of antibiotics will make pathogenic microorganisms resistant to antibiotics, and the increase of antibiotic residues in milk products will directly affect the quality of milk and indirectly affect human health.

Traditional Chinese medicine has a good effect on preventing and treating mastitis of dairy cows. Traditional Chinese medicine is able to make up for the shortage of pathogenic bacteria resistance and antibiotic residues easily caused by antibiotics, so it is favored. Although traditional Chinese medicine has the advantages of high cure rate, safety, green, no residue and no drug resistance, the traditional Chinese medicine composition for treating mastitis in dairy cows still has the disadvantage of poor efficacy, and the efficacy of traditional Chinese medicine varies greatly with different routes of administration.

SUMMARY

In view of the above technical problems, the application provides a traditional Chinese medicine ointment for preventing and treating mastitis in dairy cows and a preparation method thereof. Dandelion, herba patriniae, Caulis Lonicerae Japonicae and borneol are mixed together, and polypeptide is added to make ointment. The ointment is not only convenient for administration, but also is able to effectively overcome the first-pass effect, and gives full play to the advantages of small toxic and side effects of traditional Chinese medicine, no drug resistance and no drug residue.

In order to achieve the above purpose, the present application provides the following technical scheme.

One of the technical schemes of the application is to provide a traditional Chinese medicine ointment for preventing and treating mastitis of dairy cows. The traditional Chinese medicine ointment for preventing and treating mastitis in dairy cows includes the following raw materials in parts by mass: 20-30 parts of dandelion, 20-30 parts of herba patriniae, 10-16 parts of Caulis Lonicerae Japonicae, 0.5-1 part of borneol, 0.03-0.05 part of polypeptide, 40-50 parts of auxiliary emulsifier, 40-50 parts of liquid paraffin and 100-130 parts of white vaseline.

The amino acid sequence of the polypeptide is:

(SEQ ID NO. 1)
Phe Phe Arg Lys Val Leu Lys Leu Ile Arg Lys Ile
Trp Arg.

Optionally, the auxiliary emulsifier is glyceryl monostearate.

Optionally, the raw materials also include, in parts by mass, 0.5-1 part of antioxidant and 0.5-1 part of preservative.

Optionally, the antioxidant is alkyl gallate or butylated hydroxytoluene. The preservative is ethylparaben.

Another technical scheme of the application provides a preparation method of the traditional Chinese medicine ointment for preventing and treating mastitis in dairy cows, which includes the following steps:
S1, adding dandelion, herba patriniae and Caulis Lonicerae Japonicae into ethanol aqueous solution, extracting, and concentrating to obtain traditional Chinese medicine concentrated solution; and
S2, grinding borneol and part of liquid paraffin to eutectic mixture; adding remaining liquid paraffin and molten-state white vaseline, keeping the temperature, adding auxiliary emulsifier, stirring well, adding the traditional Chinese medicine concentrated solution and polypeptide, homogenizing, and cooling to obtain the traditional Chinese medicine ointment for preventing and treating mastitis in dairy cows.

Optionally, the volume fraction of ethanol in the ethanol aqueous solution in the S1 is 70-75%. The temperature for extracting is 80-90° C.

Ethanol aqueous solution is used as the extracting solution, which is able to effectively extract the alcohol-soluble and water-soluble components in traditional Chinese herbal medicines and enhance the anti-inflammatory effect.

Optionally, the crude drug content in the traditional Chinese medicine concentrated solution in the S1 is 1-1.5 g/ml.

Optionally, the concentrating adopts boiling concentration, so as to remove the ethanol component in the concentrated solution as much as possible and avoid damaging the activity of the polypeptide when it is mixed with the polypeptide to prepare the ointment in the later stage.

Optionally, the temperature of the molten-state white vaseline in S2 is 50-55° C. Keeping the temperature is to keep the temperature at 50-55° C.

The preparation method of the molten-state white vaseline includes the following steps: heating the white vaseline to 80-90° C., and cooling to 50-55° C. after being completely melted.

Optionally, the speed of homogenizing in S2 is 3500-4000 revolutions per minute and the time of homogenizing is 10-15 minutes.

The traditional Chinese medicinal materials used in the application are as follows.

Dandelion is cold, bitter and sweet, has effects of clearing away heat and toxic materials, relieving swelling and resolving mass, and inducing diuresis to relieve stranguria and is mainly used for treating furuncle, swollen poison, breast carbuncle, carbuncle, conjunctival congestion, sore throat, lung carbuncle, intestinal carbuncle, damp-heat jaundice, heat stranguria and astringent pain.

Herba patriniae is cool, pungent and bitter, has the effects of clearing away heat and toxic materials, eliminating phlegm and discharging pus and mainly treats intestinal carbuncle, lung carbuncle, dysentery, postpartum abdominal pain due to blood stasis, carbuncle and furuncle.

Caulis Lonicerae Japonicae is cold in nature and sweet in taste, has the effects of clearing away heat and toxic materials, expelling wind and dredging collaterals and mainly treats fever due to epidemic febrile diseases, bloody dysentery due to toxic heat, carbuncle, swelling, sores, rheumatism, arthralgia, swelling and heat pain.

Borneol is slightly cold, pungent and bitter, and fragrant, has the effects of dispersing, inducing resuscitation, clearing away heat and toxic materials, removing nebula for improving eyesight, and is mainly used for treating fever, high fever, coma, apoplexy, phlegm syncope, convulsion, epilepsy, summer-heat dampness, laryngitis, deafness, aphtha, toothache, carbuncle, hemorrhoid, red eyes, swelling and pain, and nebula covering.

Chinese veterinarians believe that mastitis in dairy cows belongs to the category of breast carbuncle. It is mostly caused by stagnation of liver qi, blood stasis of milk and accumulation of pathogenic wind and cold. Treatment should be soothing the liver and regulating qi, promoting blood circulation and clearing heat, promoting lactation and dispersing stagnation.

In the application, dandelion, herba patriniae and Caulis Lonicerae Japonicae are all capable of clearing away heat and toxic materials. Dandelion is good at resolving stagnation, especially treating breast abscess. Herba patriniae is good at removing blood stasis and pus, and treating internal abscess, and is able to play a good therapeutic role on mastitis in dairy cows together with Caulis Lonicerae Japonicae with effects of removing heat and toxic materials and treating various swelling and toxin. The added borneol is able to not only clear away heat and toxic materials, but also enhance the transdermal absorption effect of drugs when used in traditional Chinese medicine ointment. Because mastitis in dairy cows is mainly caused by pathogenic microorganisms, the polypeptide added in the application has the function of improving the sensitivity of pathogenic microorganisms to drugs, and the anti-inflammatory effect is able to be obviously improved after the polypeptide is added in the traditional Chinese medicine ointment.

The beneficial technical effects of the application are as follows:
according to the cause of mastitis in dairy cows, dandelion, herba patriniae, Caulis Lonicerae Japonicae and borneol are reasonably compatible, and all components are mutually cooperated, so that the functions of promoting blood circulation, clearing heat, promoting lactation and resolving mass are effectively exerted, and at the same time, the added polypeptide which is able to improve the drug sensitivity of pathogenic microorganisms has a very good treatment effect on mastitis in dairy cows.

The application makes the therapeutic medicines into ointment, which is not only convenient for administration, but also is able to effectively overcome the first-pass effect and give full play to the advantages of small toxic and side effects of traditional Chinese medicine, no drug resistance and no drug residue. Meanwhile, the preparation method provided by the application is simple and is beneficial to large-scale popularization.

BRIEF DESCRIPTION OF THE DRAWING

The FIGURE is a process of a preparation method of the traditional Chinese medicine ointment for preventing and treating mastitis in dairy cows.

DETAILED DESCRIPTION OF THE EMBODIMENTS

A number of exemplary embodiments of the present application will now be described in detail, and this detailed description should not be considered as a limitation of the present application, but should be understood as a more detailed description of certain aspects, characteristics and embodiments of the present application. It should be understood that the terminology described in the present application is only for describing specific embodiments and is not used to limit the present application.

In addition, for the numerical range in the present application, it should be understood that each intermediate value between the upper limit and the lower limit of the range is also specifically disclosed. Intermediate values within any stated value or stated range, as well as each smaller range between any other stated value or intermediate values within the stated range are also included in the present application. The upper and lower limits of these smaller ranges can be independently included or excluded from the range.

Unless otherwise specified, all technical and scientific terms used herein have the same meaning as commonly understood by one of ordinary skill in the art to which this application relates. Although the present application only describes the preferred methods and materials, any methods and materials similar or equivalent to those described herein may also be used in the practice or testing of the present application.

The terms "comprising", "including", "having" and "containing" used in this article are all open terms, which means including but not limited to.

Unless otherwise specified, the polypeptide mentioned in the embodiments and comparative examples of the present application all refer to polypeptide with the amino acid sequence of Phe Phe Arg Lys Val Leu Lys Leu Ile Arg Lys Ile Trp Arg (SEQ ID NO. 1), which originates from Hunan University of Science and Engineering, and the preparation technical reference publication number is CN111529683A.

As shown in the FIGURE, a process of a preparation method of the traditional Chinese medicine ointment for preventing and treating mastitis in dairy cows includes following steps:
S1, adding the dandelion, the herba patriniae and the Caulis Lonicerae Japonicae into ethanol aqueous solution, extracting, and concentrating to obtain traditional Chinese medicine concentrated solution; and S2, grinding the borneol and part of the liquid paraffin to eutectic; adding remaining liquid paraffin and molten-state white vaseline, keeping a temperature, adding the auxiliary emulsifier, stirring well, adding the traditional Chinese medicine concentrated solution and the polypeptide, homogenizing, and cooling to obtain the traditional Chinese medicine ointment for preventing and treating mastitis in dairy cows. The process will be described with reference to following embodiments.

Embodiment 1

Preparation of traditional Chinese medicine ointment for preventing and treating mastitis in dairy cows includes following steps:
- S1, taking 30 parts of dandelion, 30 parts of herba patriniae and 10 parts of Caulis Lonicerae Japonicae, adding ethanol aqueous solution with volume fraction of 75% according to the material-liquid ratio of 1:10, reflux extracting at 80° C. for 1 hour, filtering, continuing to add ethanol aqueous solution with volume fraction of 75% to filter residue according to the material-liquid ratio of 1:5, reflux extracting at 80° C. for 1 hour, filtering, combining the filtrates extracted twice, and boiling and concentrating until the crude drug content is 1.5 g/mL to obtain traditional Chinese medicine concentrated solution for later use;
- S2, heating the white vaseline to 80° C., and cooling to 50° C. after the white vaseline is completely melted to obtain the molten-state white vaseline for later use; and
- S3, taking 0.5 part of borneol, adding 10 parts of liquid paraffin, and grinding to eutectic mixture; adding the remaining 30 parts of liquid paraffin and 100 parts of molten-state white vaseline obtained in step (2), keeping the temperature of the mixture at 50-55° C., adding 40 parts of glyceryl monostearate, stifling well, then adding the traditional Chinese medicine concentrated solution obtained in step (1), 0.05 part of polypeptide, 0.5 part of alkyl gallate and 0.5 part of ethylparaben, homogenizing at 3500 revolutions per minute for 15 minutes, cooling to room temperature to obtain the traditional Chinese medicine ointment for preventing and treating mastitis in dairy cows.

Embodiment 2

Preparation of traditional Chinese medicine ointment for preventing and treating mastitis in dairy cows includes following steps:
- S1, taking 25 parts of dandelion, 25 parts of herba patriniae and 16 parts of Caulis Lonicerae Japonicae, adding ethanol aqueous solution with volume fraction of 75% according to the material-liquid ratio of 1:10, reflux extracting at 80° C. for 1 hour, filtering, continuing to add ethanol aqueous solution with volume fraction of 75% to filter residue according to the material-liquid ratio of 1:5, reflux extracting at 80° C. for 1 hour, filtering, combining the filtrates extracted twice, and boiling and concentrating until the crude drug content is 1.0 g/mL to obtain traditional Chinese medicine concentrated solution for later use;
- S2, heating the white vaseline to 80° C., and cooling to 50° C. after the white vaseline is completely melted to obtain the molten-state white vaseline for later use; and
- S3, taking 0.7 part of borneol, adding 10 parts of liquid paraffin, and grinding to eutectic mixture; adding the remaining 35 parts of liquid paraffin and 120 parts of molten-state white vaseline obtained in step (2), keeping the temperature of the mixture at 50-55° C., adding 50 parts of glyceryl monostearate, stifling well, then adding the traditional Chinese medicine concentrated solution obtained in step (1), 0.03 part of polypeptide, 0.5 part of alkyl gallate and 1 part of ethylparaben, homogenizing at 3500 revolutions per minute for 15 minutes, cooling to room temperature to obtain the traditional Chinese medicine ointment for preventing and treating mastitis in dairy cows.

Embodiment 3

Preparation of traditional Chinese medicine ointment for preventing and treating mastitis in dairy cows includes following steps:
- S1, taking 25 parts of dandelion, 20 parts of herba patriniae and 14 parts of Caulis Lonicerae Japonicae, adding ethanol aqueous solution with volume fraction of 70% according to the material-liquid ratio of 1:10, reflux extracting at 90° C. for 1 hour, filtering, continuing to add ethanol aqueous solution with volume fraction of 70% to filter residue according to the material-liquid ratio of 1:5, reflux extracting at 90° C. for 1 hour, filtering, combining the filtrates extracted twice, and boiling and concentrating until the crude drug content is 1.2 g/mL to obtain traditional Chinese medicine concentrated solution for later use;
- S2, heating the white vaseline to 90° C., and cooling to 50° C. after the white vaseline is completely melted to obtain the molten-state white vaseline for later use;
- S3, taking 1 part of borneol, adding 15 parts of liquid paraffin, and grinding to eutectic mixture; adding the remaining 35 parts of liquid paraffin and 130 parts of molten-state white vaseline obtained in step (2), keeping the temperature of the mixture at 50-55° C., adding 45 parts of glyceryl monostearate, stirring well, then adding the traditional Chinese medicine concentrated solution obtained in step (1), 0.05 part of polypeptide, 1 part of alkyl gallate and 0.5 part of ethylparaben, homogenizing at 4000 revolutions per minute for 10 minutes, cooling to room temperature to obtain the traditional Chinese medicine ointment for preventing and treating mastitis in dairy cows.

COMPARATIVE EXAMPLE 1

Preparation of traditional Chinese medicine ointment for preventing and treating mastitis in dairy cows:

Compared with embodiment 1, the difference is that the addition of polypeptide is omitted, and other steps are the same as embodiment 1.

Effect Verification:

Fifty dairy cows with mastitis detected by Shanghai Mastitis Test (SMT) are selected from a dairy farm in Hunan Province, of which 20 cows are externally coated with the traditional Chinese medicine ointment for preventing and treating mastitis in dairy cows prepared in embodiment 1 and 20 cows are externally applied with the traditional Chinese medicine ointment for preventing and treating mastitis in dairy cows prepared in comparative example 1, with the dosage of 2 g each time, twice a day for 5 days. The remaining 10 cows are perfused with penicillin 100,000 IU after all the milk is discharged from their breasts, as a control group.

Cure standard: one day after stopping the ointments, if curdled milk is negative by the sodium hydroxide test, the cows are judged to be cured.

The therapeutic effects of each experimental group are shown in Table 1.

TABLE 1

The therapeutic effects of each experimental group

| Experimental group | Dairy cows (head) with mastitis | Cows (head) with curdled milk being negative by sodium hydroxide test | Cure rate (%) |
|---|---|---|---|
| Embodiment 1 group | 20 | 18 | 90 |
| Comparative example 1 group | 20 | 14 | 70 |
| Control group | 10 | 8 | 80 |

As can be seen from Table 1, the added polypeptide is able to obviously improve the therapeutic effect of traditional Chinese medicine composition, which may be because the added polypeptide is able to improve the sensitivity of pathogenic microorganisms to traditional Chinese medicine extracts, so the therapeutic effect of the prepared traditional Chinese medicine ointment is able to be obviously improved after the added polypeptide is added.

In order to confirm the above conjecture, the application verifies the antibacterial effect of the traditional Chinese medicine concentrated solution prepared in each embodiment, and the method is as follows:
(1) taking Staphylococcus aureus and Escherichia coli grown on ordinary nutrient agar plates, dipping a small number of colonies with an inoculating loop, inoculating colonies into 5 mL of Mueller-Hinton (MH) broth, and performing shake culture at 37° C. for 6 hours at 200 r/min; taking bacterial liquid in logarithmic growth period and diluting the bacterial liquid with sterilized physiological saline until the bacterial content is 1-2× 108 CFU/ml; diluting with sterilized physiological saline for 1000 times for later use;
(2) making a round filter paper with a diameter of 6.5 mm with a puncher, and dry-heat sterilizing it; first, evenly inoculating the bacterial liquid obtained in step (1) into a nutrient agar culture dish, then attaching the sterilized round filter paper to the surface of agar, transferring 20 μL of liquid medicine (diluted by 10 times) with a micropipette gun, dropping the liquid medicine in the center of the round filter paper, culturing it at 37° C. for 24 hours, and measuring the diameter of the bacteriostatic circle in which different liquid medicines are dropped. The results are shown in Table 2.

TABLE 2

Diameter of bacteriostatic circle in different liquid medicine groups

| Liquid medicine (transferring 20 μL after diluting by 10 times) | Diameter of bacteriostatic circle of Staphylococcus aureus (mm) | Diameter of bacteriostatic circle of Escherichia coli (mm) |
|---|---|---|
| Traditional Chinese medicine concentrated solution in embodiment 1 Group | 8.3 | 7.8 |
| Traditional Chinese medicine concentrated solution in embodiment 1 Group + 0.05 g of polypeptide | 23.9 | 21.5 |
| Traditional Chinese medicine concentrated solution in embodiment 2 Group | 7.6 | 7.9 |
| Traditional Chinese medicine concentrated solution in embodiment 2 Group + 0.03 g of polypeptide | 21.1 | 21.6 |
| Traditional Chinese medicine concentrated solution in embodiment 3 Group | 8.4 | 8.2 |
| Traditional Chinese medicine concentrated solution in embodiment 3 Group + 0.05 g of polypeptide | 22.4 | 21.9 |
| Solution with polypeptide content of 1 mg/mL | 15.3 | 14.7 |

As can be seen from Table 2, the simple polypeptide solution has a strong antibacterial effect, but it is able to obviously improve the antibacterial effect of the traditional Chinese medicine concentrated solution for treating mastitis of dairy cows after being added to the traditional Chinese medicine concentrated solution for treating mastitis, indicating that the polypeptide added in the application is able to synergize with the traditional Chinese medicine concentrated solution disclosed by the application and has a stronger antibacterial effect.

The above-mentioned embodiments only describe the preferred mode of the application, and do not limit the scope of the application. Under the premise of not departing from the design spirit of the application, various modifications and improvements made by ordinary technicians in the field to the technical scheme of the application shall fall within the protection scope determined by the claims of the application.

What is claimed is:

1. A traditional Chinese medicine ointment for preventing and treating mastitis in dairy cows, comprising the following raw materials in parts by weight: 20-30 parts of dandelion, 20-30 parts of herba Patriniae, 10-16 parts of caulis Lonicerae japonicae, 0.5-1 part of borneol, 0.03-0.05 parts of polypeptide, 40-50 parts of auxiliary emulsifier, 40-50 parts of liquid paraffin, 0.5-1 parts of antioxidant, and 0.5-1 parts of preservative; wherein the amino acid sequence of the polypeptide is SEQ ID NO: 1.

2. The traditional Chinese medicine ointment for preventing and treating mastitis in dairy cows according to claim 1, wherein the auxiliary emulsifier is glyceryl monostearate.

3. The traditional Chinese medicine ointment for preventing and treating mastitis in dairy cows according to claim 1, wherein the antioxidant is alkyl gallate or butylated hydroxytoluene; and the preservative is ethylparaben.

* * * * *

SEQUENCE LISTING

```
Sequence total quantity: 1
SEQ ID NO: 1            moltype = AA   length = 14
FEATURE                 Location/Qualifiers
source                  1..14
                        mol_type = protein
                        organism = synthetic construct
SEQUENCE: 1
FFRKVLKLIR KIWR                                                       14
```